United States Patent [19]

Shukla

[11] 4,233,973

[45] Nov. 18, 1980

[54] APPARATUS FOR ADMINISTERING INTRAVENOUS DRUGS

[76] Inventor: Vishnu S. Shukla, c/o Newcastle General Hospital, Department of Radiation and Oncology, Westgate Rd., Newcastle upon Tyne NE4 6BE, England

[21] Appl. No.: 37,957

[22] Filed: May 9, 1979

[30] Foreign Application Priority Data

May 12, 1978 [GB] United Kingdom ............... 19155/78

[51] Int. Cl.$^3$ .......................... A61M 5/00; A61J 1/00
[52] U.S. Cl. ............... 128/214 R; 128/272.1
[58] Field of Search ............ 128/214 R, 214.2, 214.4, 128/272.1, 218 M, 215

[56] References Cited

U.S. PATENT DOCUMENTS

| 966,591 | 8/1910 | Payne | 128/214 R |
|---|---|---|---|
| 1,517,849 | 12/1924 | McLellan | 128/214.2 |
| 3,332,421 | 7/1967 | King et al. | 128/218 M |
| 3,397,694 | 8/1968 | Ogle | 128/218 M |
| 3,650,093 | 3/1972 | Rosenberg | 128/214.2 |
| 3,844,283 | 10/1974 | Dabney | 128/214 R |

FOREIGN PATENT DOCUMENTS 715653 9/1931 Fed. Rep. of Germany ...... 128/214 R

Primary Examiner—Robert W. Michell
Assistant Examiner—T. J. Wallen

[57] ABSTRACT

Apparatus for administering intravenously a drug supplied initially in powdery form, in particular cytotoxic drugs, said apparatus comprising a sealed container for the drug, an infusion set supplying a drip feed of intravenous liquid to the patient and also being in communication with the interior of said sealed container, and a piston-cylinder pump assembly also in communication with the interior of said container in such a manner that appropriate actuation of the pump assembly can first of all draw intravenous liquid from the infusion set into the container to dissolve the drug into solution and thereafter can feed a controlled volume of said solution from the container to the patient. The apparatus thereby provides a closed circuit for the drug which can be administered without removing from the circuit any component containing or transporting the drug. The apparatus can readily be made opaque thereby avoiding photodegradation of photosensitive drugs being administered.

10 Claims, 3 Drawing Figures

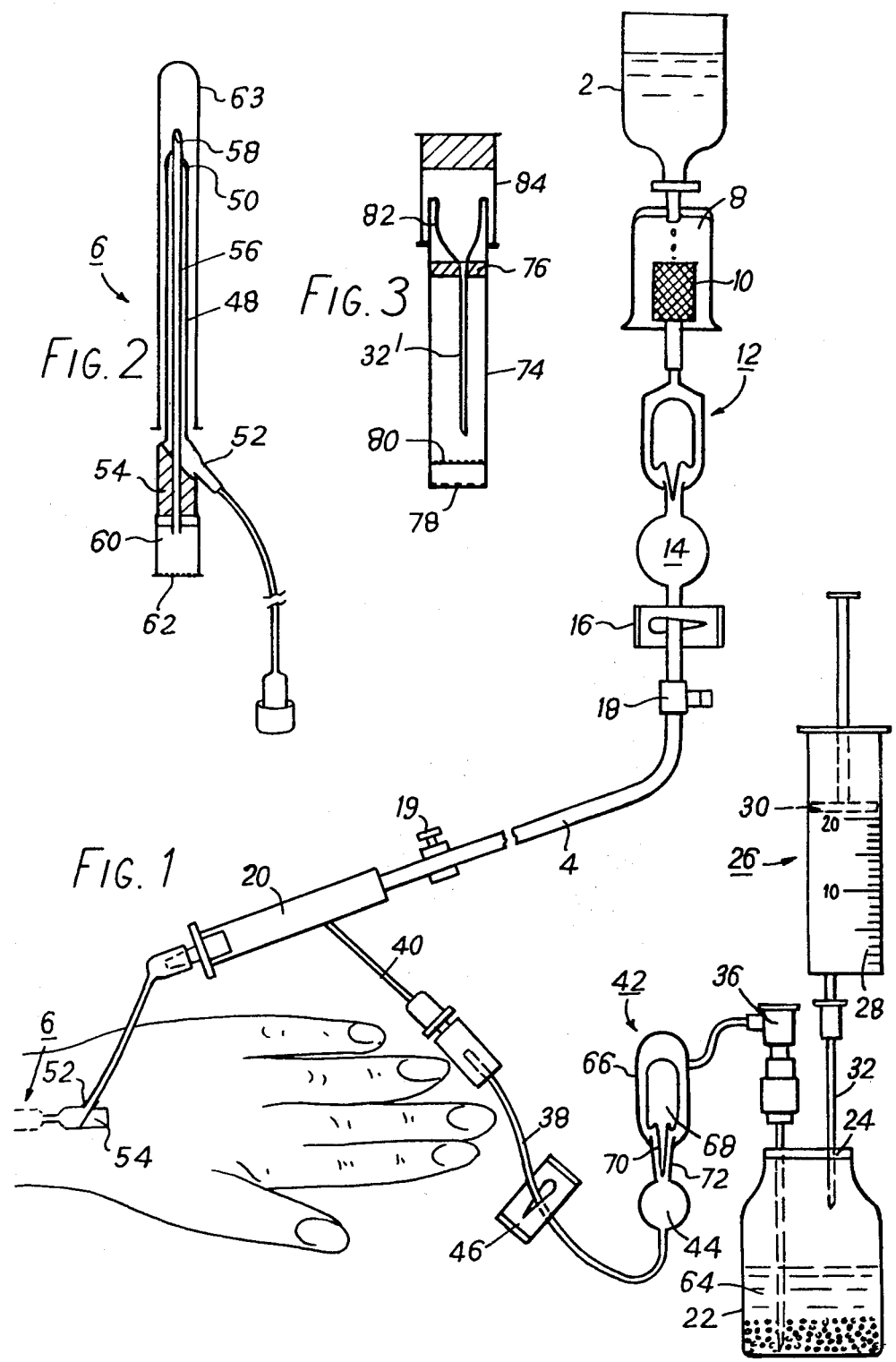

APPARATUS FOR ADMINISTERING INTRAVENOUS DRUGS

BACKGROUND OF THE INVENTION

This invention relates to apparatus for administering intravenous drugs to a patient, in particular drugs supplied in powdery form.

When administering intravenously to a patient a drug initially supplied in powdery form, where the individual particles are either loose or compacted into cake form, such as a cytotoxic agent for treating cancer, a standard procedure is currently adopted. This procedure involves providing a sealed container holding the powdery drug and injecting into the bottle, by way of a standard syringe and hypodermic needle, a volume of intravenously-acceptable liquid in which the drug will dissolve. The container is then shaken until the drug is dissolved and a solution is formed.

A volume of air equal to that of the previously injected liquid is then drawn into the syringe and is injected into the container to equalise the pressures in the syringe and the container, and the desired volume of liquid medicament is drawn into the syringe.

Said syringe is then removed from the container and the drug is injected into the patient.

Such a procedure has a number of disadvantages, the administrator of the drug being particularly prone to possible exposure to the drug. For example, the needle of the syringe may accidentally be removed from the body of the syringe during charging of said syringe; the needle may be accidentally removed from the container during said charging; the supposedly fluid-tight rubber stopper on the container may develop a leak after removal therefrom of the needle.

In all such cases there is a possibility of the drug contacting or entering the doctor or nurse administering the drug—whereas cytotoxic drugs can successfully treat a patient with cancer, most of them are known to be cancer-producing agents as well. Thus it will be appreciated that the problems are of some significance.

Furthermore, many cytotoxic agents and other drugs are photosensitive in that any, or extended exposure to light causes degradation of the drugs, rendering them substantially less effective and some of them more toxic, e.g. Dacarbazine.

When administering such photosensitive drugs by means of the above-detailed procedure, it has become standard practice to wrap the syringe in silver foil or dark paper to eliminate light and to inject the drug into a patient in a dark room. Clearly such a procedure leaves the doctor or nurse particularly prone to accidental exposure to the drug, and the drug open to possible contamination by hospital ward bacteria.

As is always the case when administering drugs to a patient, it is advisable, if not essential, that all the apparatus used is sterile and that no bacteria or the like is contained within the drug itself. This is particularly important as regards patients being treated with cytotoxic agents as such treatment reduces substantially the patient's general immunity and the presence of any bacteria in the drug can have drastic effects.

In the above-detailed established procedure for injecting drugs using a standard syringe and hypodermic needle, it will be appreciated that it is necessary to bubble air through the solution to equalise the pressures in the syringe and container. If, as is common practice, the air used is from a hospital ward atmosphere, the problem of bacteria is particularly prevalent. This is because such atmospheres carry resistant strains of bacteria and therefore are more likely to cause problems on immunodepressed patients.

SUMMARY OF THE INVENTION

An object of the present invention is to provide a closed circuit apparatus for administering drugs initially provided in powdery form in a manner which substantially reduces or eliminates the possibility of exposure of the person administering the drug.

The invention also provides an apparatus which is readily adaptable to the administration of photosensitive drugs without increasing the possibility of exposure of the person administering the drug, and which can ensure the sterility of the administered drug.

In summary, the invention provides apparatus for administering intravenously a drug supplied in powdery form, the apparatus comprising an intravenous infusion set including a venipuncture member for feeding intravenous liquid into a patient's vein, a sealed container for the powdery drug, pump means for controlling the flow of fluid to and from the sealed container, said pump means including a piston-cylinder assembly, the cylinder of which is in communication with the upper regions of the sealed container, and a tubular member extending from the lower regions of said container to communicate into the drip feed of the intravenous liquid to the patient, the arrangement being such that withdrawal of the piston in the cylinder of the pump means partially evacuates the sealed container, the removed gaseous content of said container being replaced by intravenous liquid fed under gravity from the infusion set to dissolve the powdery drug into solution, controlled return movement of the piston in the cylinder of the pump means forcing a controlled volume of solution from the sealed container through the tubular member to the infusion set whereby said solution, together with the intravenous liquid from the infusion set, is fed by the venipuncture member to the patient.

Such apparatus provides a closed system for the drug to be administered whereby initial mixing of the powdery drug into solution and the subsequent injection of the dissolved drug into the patient are achieved without removing from the system any component of the apparatus containing or supplied with the drug, the preparation of the solution and the injection thereof being under the control of the pump means, conveniently a standard injection syringe.

Clearly such an arrangement overcomes the problem of exposure of the administrator, while photodecomposition of a photosensitive drug can readily be prevented by making the sealed container and tubular member opaque or by covering the apparatus with a dark cloth during administration.

BRIEF DESCRIPTION OF THE DRAWINGS

FIG. 1 illustrates apparatus according to the invention;

FIG. 2 illustrates a venipuncture member of apparatus according to the invention, and FIG. 3 illustrates a needle provided with a bacterial filtration arrangement for use with apparatus according to the invention.

DETAILED DESCRIPTION OF THE PREFERRED EMBODIMENT

Referring to the drawings, the illustrated apparatus comprises an intravenous infusion set including a container 2, either a bottle or a container of the collapsible-bag type, of intravenous liquid connected by means of a length of flexible plastics tubing 4 with a venipuncture member indicated generally at 6.

Between the container 2 and the member 6 are a drip chamber 8 which may or may not contain a filter 10, a safety valve indicated generally at 12 for reasons to be detailed below, a flexible bubble member 14 associated with the valve 12 again for reasons to be detailed below, a pinch clip 16, a first injection site 18, a flow-control clamp 19 for the drip feed and a second injection site 20 in the form of a length of self-sealing latex rubber tubing.

The apparatus further comprises a container 22 sealed by a rubber stopper 24 in which container is a volume of powdery drug, for example a cytotoxic drug, to be administered to a patient.

A standard injection syringe 26 includes a cylindrical body member 28 and a piston 30, the outlet from the body member 28 having attached thereto a standard hypodermic needle 32. The needle 32 extends through the stopper 24 of the container to terminate within the upper regions of said container.

A further longer hollow metal needle 34 also extends through the stopper 24 to terminate adjacent the bottom of the container 22, the upper end of said needle having attached thereto, by means of a connecting piece 36, one end of a further length of flexible plastics tubing 38. The other end of said tubing carries a still further hollow metal needle 40 which may be a standard hypodermic needle.

Between the connecting piece 36 and the needle 40 are located a further safety valve 42 and associated flexible bubble member 44 for reasons to be detailed below, and a further pinch clip 46.

The venipuncture member 6 includes a flexible cannula 48 having a bevelled one end 50, a side arm 52 communicating into the bore of the cannula extending from the other end of said cannula. Positioned adjacent said other end of the cannula 48 is a plug 54 of latex rubber forming an extension of said cannula, while a hollow metal needle 56 extends through said plug 54, through the bore of said cannula 48 to terminate in a one end 58 located just beyond the one end 50 of the cannula 48. The other end of the needle 56 carries a transparent chamber 60 releasably attachable to the plug 54 to form a continuation of the cannula 48, said chamber being provided with a porous end cover 62. The venipuncture member 6 is housed within a protective sheath 63.

When attaching the venipuncture member 6 to a patient, the sheath 63 is removed therefrom and the ends 50, 58 of the cannula 48 and needle 56 respectively are pushed into a vein of the patient. Once the needle 56 is in the vein, blood flows through said needle to the transparent chamber 60 where it can be seen by the doctor or nurse. The needle 56 and attached chamber 60 are then bodily removed from the venipuncture member to leave the cannula only in the vein, and the drip feed from the infusion set, which has previously been evacuated, is started.

Before administering the powdery drug in the container 22, it is first of all necessary to dissolve this drug into solution. This is achieved by locating the free end of the needle 40 into the latex rubber tubing of the injection site 20 contained in the infusion set, and puncturing the stopper 24 with the needle 32 attached to the syringe 26, with the piston 30 fully depressed into the cylindrical body member 28.

With the needle 34 extending to the lower regions of the container 22, the piston 30 is withdrawn in the body member 28 to withdraw a predetermined volume of bacteria-free air from the container 22. The pressure in said container thus falls, and intravenous liquid from the container 2, whilst continuing to flow to the patient, also flows under gravity through the needle 40, the tubing 38, the connecting piece 36 and the needle 34 into said container to replace the removed air.

The container 22 can then be shaken to dissolve the drug into a solution 64, the pressures in the container 22 and the syring 26 being equal.

Some or all of the solution 64 is then administered to the patient by depressing the piston 30 in the body member 28 of the syringe 26 to return the previously withdrawn bacteria-free air into the container 22 and thereby force an equivalent volume of solution from the container through the needle 34, tubing 38 and needle 40 into the drip feed from the infusion set and thence to the venipuncture member 6 and into the patient.

The valve 42 in the tubing 38 comprises a transparent inspection chamber 66 in which is housed a float member 68. The float member 68 is such as, with the chamber 66 filled with liquid, to float at a midway position in said chamber with a closure portion 70 of the member 68 permitting liquid flow through an outlet 72 from the chamber 66. If air flows from the container 22 through the needle 34, it collects in the upper regions of the chamber 66, and the level of liquid in the container falls. When said chamber is full of air, the float member falls into a lowermost position sealing off the outlet 72 from the chamber. Thus no air is allowed to flow past the valve 42 and into the vein of the patient.

Any air in the chamber 66 can be sucked back into the container 22 by means of the syringe 26. If the float member 68 should stick in its lowermost position, the bubble member 44, which always contains liquid, can be squeezed (after clipping the tube 38 with the pinch clip 46) to release said member 68.

It will be appreciated that the valve 12 and bubble member 14 can be used in a similar way to prevent the passage of air from the container 22 to the venipuncture member 6 and to release the float member of said valve should it stick in its lowermost position.

If the capacity of the syringe 26 is less than that of the desired volume of the comfortably-dissolved solution of the drug to be administered, the bacterial filtration arrangement shown in FIG. 3 may be used to ensure that all air entering the container 22 to force solution 64 to a patient is bacteria free. More particularly, the solution is made up as detailed above but by withdrawing the bacteria-free air from the container 22 in two or more stages by means of the syringe 26—i.e. the needle 32 is inserted through the stopper 24, a volume of air is withdrawn into the syringe and the syringe is removed from the container 22. This air is then discharged from the syringe, the needle 32 is reinserted through the stopper 24 and a further volume of bacteria-free air is withdrawn into said syringe.

Any air in addition to this further volume of air needed to force the dissolved drug to the patient should be bacteria free. Thus, once said further volume of bacteria-free air in the syringe has been returned into the container, the syringe 26 and needle 32 are withdrawn from the container 22, the needle 32 is removed from the syringe 26 and the needle/filter of FIG. 3 is attached to said syringe. More particularly, FIG. 3 illustrates a cylindrical housing 74 adjacent one end of which is a rubber plug 76 and the other end of which comprises an apertured plastics grid 78. Within the housing 74, adjacent the other end thereof, is a bacterial filter element 80. A standard hypodermic needle 32' projects through the plug 76 into the housing 74, the upper end of said needle carrying a standard female adaptor 82 to permit attachment of said needle to a standard injection syringe. A cap 84 closes the one end of the housing 74.

Thus it will be appreciated that, on removal of the cap 84 and on attachment of the needle 32' to the syringe 26, any air drawn into the syringe 26 through said needle 32' will be free from bacteria, said bacteria being removed therefrom by the filter element 80. The syringe 26 and needle 32' are then withdrawn from the housing 74 and the bacteria-free air in the body member 28 of the syringe can be injected into the container 22 to effect the administration of a further volume of drug to the patient.

The provision of a length of flexible tubing between the venipuncture member 6 and the injection site 20 to locate said site remote from a patient, together with the provision of the side arm 52 extending laterally from the cannula, substantially reduces, compared with established arrangements, the axial extent of venipuncture means actually in and adjacent the patient, enabling more comfortable movement of the patient's hand—in established arrangements, an injection site in the form of a rubber flash ball commonly forms an extension of the venipuncture member.

The provision of the injection site 18 in the drip feed set enables drugs additional to that in the container 22 to be readily injected into the patient without excessively puncturing the site 20 which may result in leakage of the drug onto the arm of a patient.

If a drug to be administered to a patient as a solution 64 is photosensitive in nature, photodegradation of such a drug can readily be avoided by making opaque the components of the apparatus which contain or transport the solution, in particular the container 22 and all tubing associated therewith. Additionally, the infusion set can also be made opaque to prevent photodegradation of any of the photosensitive drug that may be drawn or pushed into it during use of the apparatus although a chamber of the safety valve can be kept transparent to enable entry of air into the set to be viewed.

It is to be appreciated that, in common with established practice, all components of the apparatus described and illustrated are provided in sterile packs and all air within said components is initially bacteria free.

Apparatus according to the invention provides a closed-circuit system whereby a drug, for example a photosensitive cytotoxic drug, can, once the apparatus is set up, be administered to a patient under the control of pump means, for example a standard medical injection syringe, and without the necessity to remove from the system any component containing or supplied with the drug in question. Clearly such an arrangement substantially eliminates the possibility of the person administering the drug from being exposed thereto whilst at the same time facilitating the administration.

The pump means may be other than a medical injection syringe and may be other than manually operated, for example mechanically or electrically operated.

What I claim and desire to secure by Letters Patent is:

1. Apparatus for administering intravenously a drug supplied in powdery form, the apparatus comprising an intravenous infusion set having a drip feed including a venipuncture member for feeding intravenous liquid into a patient's vein, a sealed container for the powdery drug, pump means for controlling the flow of fluid to and from the sealed container, said pump means including a piston-cylinder assembly, the cylinder of which is in communication with the upper regions of the sealed container, and a tubular member extending from the lower regions of said container to communicate into the drip feed of the intravenous liquid to the patient, the arrangement being such that withdrawal of the piston in the cylinder of the pump means partially evacuates the sealed container, the removed gaseous content of said container being replaced by intravenous liquid fed under gravity from the infusion set to dissolve the powdery drug into solution, controlled return movement of the piston in the cylinder of the pump means forcing a controlled volume of solution from the sealed container through the tubular member to the infusion set whereby said solution, together with the intravenous liquid from the infusion set, is fed by the venipuncture member to the patient.

2. Apparatus as claimed in claim 1 in which the pump means comprises a medical injection syringe.

3. Apparatus as claimed in claim 2 and including a stopper of a resilient, self-sealing material sealing the container, and a rigid hollow needle one end of which is attached to the syringe, said needle extending through said stopper, the other end of the needle being located in the upper regions of said container.

4. Apparatus as claimed in claim 3 in which the tubular member includes a rigid, hollow needle extending from the lower regions of the container, through the upper regions of said container, through said stopper to the exterior of the container, and a length of flexible tubing from the upper end of said needle to the venipuncture member.

5. Apparatus as claimed in claim 4 and including a safety valve in the length of flexible tubing between the upper end of said needle and the venipuncture member to prevent air passing from the sealed container to the venipuncture member.

6. Apparatus as claimed in claim 1 in which the venipuncture member includes a flexible cannula one end of which is for location in a patient's vein and the other end of which is adapted for attachment to both the infusion set and the tubular member extending from the lower regions of the container.

7. Apparatus as claimed in claim 6 in which the infusion set includes a further length of tubing, an extent of resilient, self-sealing material being contained within said further length of tubing, a hollow arm member being provided at the other end of the cannula to extend substantially laterally from said cannula, said further length of tubing being attached to said arm member, a rigid hollow needle attached to the end of the tubular member remote from the sealed container, said needle having a free end projecting through the material of, into the bore of, said extent of resilient, self-sealing material.

8. Apparatus as claimed in claim 7 in which a plug of a resilient self-sealing material closes the other end of the cannula, and a transparent chamber forms an extension of said other end of the cannula, the venipuncture member further comprising a rigid, hollow needle extending through the plug and through the bore of the cannula to terminate in a one end projecting just beyond the one end of the cannula, the other end of said needle being located within said transparent chamber.

9. Apparatus as claimed in claim 1 and including a safety valve in the infusion set between a source of intravenous liquid in said set and the venipuncture member.

10. Apparatus as claimed in claim 1 in which the container and at least that part of the tubular member between the container and the venipuncture member are opaque.

* * * * *